(12) United States Patent
Lentz et al.

(10) Patent No.: US 7,637,903 B2
(45) Date of Patent: Dec. 29, 2009

(54) CATHETER ARTICULATION SEGMENT WITH ALTERNATING CUTS

(75) Inventors: David J. Lentz, La Jolla, CA (US); Richard J. Koerner, San Diego, CA (US)

(73) Assignee: Cryocor, Inc., San Diego, CA (US)

( * ) Notice: Subject to any disclaimer, the term of this patent is extended or adjusted under 35 U.S.C. 154(b) by 183 days.

(21) Appl. No.: 10/872,612

(22) Filed: Jun. 21, 2004

(65) Prior Publication Data

US 2005/0177132 A1    Aug. 11, 2005

Related U.S. Application Data

(63) Continuation-in-part of application No. 10/774,665, filed on Feb. 9, 2004, now abandoned.

(51) Int. Cl.
*A61M 25/00* (2006.01)
(52) U.S. Cl. ........................ 604/525; 604/523
(58) Field of Classification Search ............. 604/525, 604/95.01–95.05, 523, 264, 96.01, 103.08; 606/191, 194
See application file for complete search history.

(56) References Cited

U.S. PATENT DOCUMENTS

| | | | |
|---|---|---|---|
| 1,060,665 A | 5/1913 | Bell | |
| 2,574,840 A | 11/1951 | Pieri et al. | |
| 3,547,103 A | 12/1970 | Cook | |
| 3,605,725 A | 9/1971 | Bentov | |
| 3,906,938 A | 9/1975 | Fleischhacker | |
| 4,215,703 A | 8/1980 | Willson | |
| 4,245,624 A | 1/1981 | Komiya | |
| 4,456,017 A | 6/1984 | Miles | |
| 4,582,181 A | 4/1986 | Samson | |
| 4,586,923 A | 5/1986 | Gould et al. | |

(Continued)

FOREIGN PATENT DOCUMENTS

EP        0778040        6/1997

(Continued)

OTHER PUBLICATIONS

Boston Scientific Corporation, Synchro Guidewires-Neurovascular Access Product Brochure, 2003, pp. 1-4.

(Continued)

*Primary Examiner*—Nicholas D Lucchesi
*Assistant Examiner*—Laura A Bouchelle
(74) *Attorney, Agent, or Firm*—Darby & Darby PC; Patrick R. Turner

(57) ABSTRACT

An articulation segment for a catheter includes a tube formed with a first plurality of axially aligned slits that are respectively oriented in planes perpendicular to the axis, with each slit extending azimuthally in an arc partway around the axis. The tube is also formed with a second plurality of similarly formed slits that are axially offset and diametrically opposed relative to the slits of the first plurality to allow for a bending of the catheter in a plurality of different planes. In a particular embodiment, the slits are arranged to allow the articulation segment to be reconfigured from a straight, substantially cylindrically shaped tube to a configuration in which a portion of the articulation segment is formed in the shape of a ring.

11 Claims, 3 Drawing Sheets

U.S. PATENT DOCUMENTS

| | | | |
|---|---|---|---|
| 4,757,827 A | 7/1988 | Buchbinder et al. | |
| 4,813,434 A | 3/1989 | Buchbinder et al. | |
| 4,815,478 A | 3/1989 | Buchbinder et al. | |
| 4,886,067 A | 12/1989 | Palermo | |
| 4,935,025 A | 6/1990 | Bundy et al. | |
| 4,960,134 A | 10/1990 | Webster, Jr. | |
| 4,960,411 A | 10/1990 | Buchbinder | |
| 4,976,688 A | 12/1990 | Rosenblum | |
| 5,037,391 A | 8/1991 | Hammerslag et al. | |
| 5,042,985 A | 8/1991 | Elliott et al. | |
| 5,108,368 A | 4/1992 | Hammerslag et al. | |
| 5,114,414 A | 5/1992 | Buchbinder | |
| 5,125,895 A | 6/1992 | Buchbinder et al. | |
| 5,190,050 A | 3/1993 | Nitzsche | |
| 5,242,441 A | 9/1993 | Avitall | |
| 5,318,525 A | 6/1994 | West et al. | |
| 5,322,064 A * | 6/1994 | Lundquist | 600/381 |
| 5,329,923 A | 7/1994 | Lundquist | |
| 5,330,466 A | 7/1994 | Imran | |
| 5,334,145 A | 8/1994 | Lundquist et al. | |
| 5,368,564 A | 11/1994 | Savage | |
| 5,449,343 A | 9/1995 | Samson et al. | |
| 5,507,725 A | 4/1996 | Savage et al. | |
| 5,656,030 A | 8/1997 | Hunjan et al. | |
| 5,715,817 A | 2/1998 | Stevens-Wright et al. | |
| 5,906,590 A | 5/1999 | Hunjan et al. | |
| 5,928,191 A | 7/1999 | Houser et al. | |
| 5,944,689 A | 8/1999 | Houser et al. | |
| 6,013,052 A | 1/2000 | Durman et al. | |
| 6,066,125 A | 5/2000 | Webster, Jr. | |
| 6,106,518 A | 8/2000 | Wittenberger et al. | |
| 6,123,699 A | 9/2000 | Webster, Jr. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,254,568 B1 | 7/2001 | Ponzi | |
| 6,267,746 B1 | 7/2001 | Bumbalough | |
| 6,319,248 B1 | 11/2001 | Nahon | |
| 6,332,880 B1 | 12/2001 | Yang et al. | |
| 6,346,099 B1 | 2/2002 | Altman | |
| 6,413,234 B1 | 7/2002 | Thompson et al. | |
| 6,440,126 B1 | 8/2002 | Abboud et al. | |
| 6,468,260 B1 | 10/2002 | Bumbalough et al. | |
| 6,485,455 B1 | 11/2002 | Thompson et al. | |
| 6,500,167 B1 | 12/2002 | Webster, Jr. | |
| 6,522,933 B2 | 2/2003 | Nguyen | |
| 6,540,725 B1 | 4/2003 | Ponzi | |
| 6,551,271 B2 | 4/2003 | Nguyen | |
| 6,569,114 B2 | 5/2003 | Ponzi et al. | |
| 6,569,158 B1 | 5/2003 | Abboud et al. | |
| 6,571,131 B1 | 5/2003 | Nguyen | |
| 6,579,278 B1 | 6/2003 | Bencini | |
| 6,585,717 B1 * | 7/2003 | Wittenberger et al. | 604/523 |
| 6,585,718 B2 | 7/2003 | Hayzelden et al. | |
| 6,602,278 B1 | 8/2003 | Thompson et al. | |
| 6,605,086 B2 | 8/2003 | Hayzelden et al. | |
| 6,607,505 B1 | 8/2003 | Thompson et al. | |
| 6,610,058 B2 | 8/2003 | Flores | |
| 6,623,448 B2 * | 9/2003 | Slater | 604/95.01 |
| 2001/0025075 A1 | 9/2001 | Smith et al. | |
| 2002/0025998 A1 | 2/2002 | McCullough et al. | |
| 2002/0111618 A1 * | 8/2002 | Stewart et al. | 606/41 |
| 2003/0004539 A1 | 1/2003 | Linder et al. | |

FOREIGN PATENT DOCUMENTS

| | | |
|---|---|---|
| WO | WO-9911313 | 3/1999 |
| WO | WO-03004086 | 1/2003 |
| WO | WO-2004047899 | 6/2004 |

OTHER PUBLICATIONS

Boston Scientific Corporation, Guidewires Selection Guide, 2003, pp. 1-2.

* cited by examiner

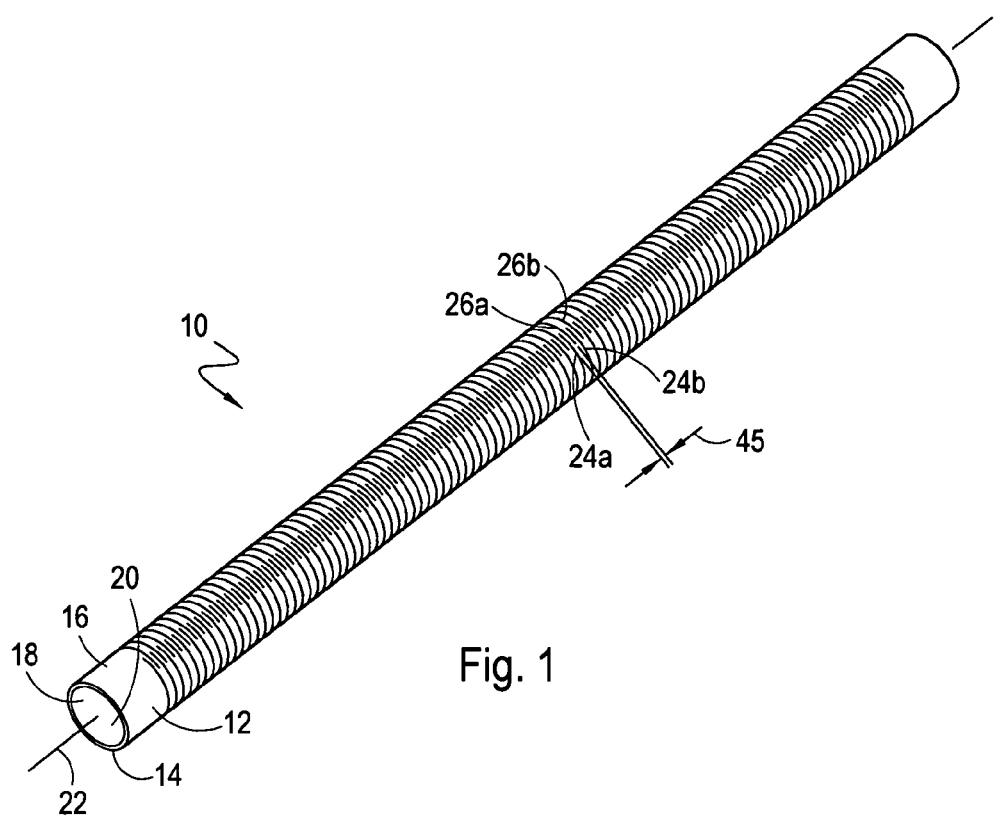
Fig. 1
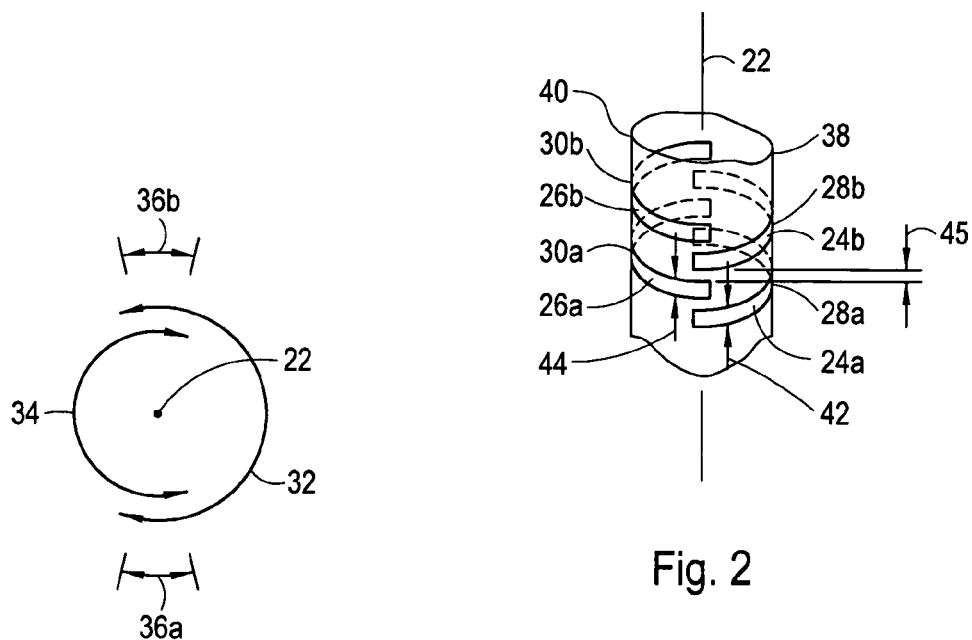
Fig. 3
Fig. 2

CATHETER ARTICULATION SEGMENT WITH ALTERNATING CUTS

This application is a continuation-in-part of application Ser. No. 10/774,665 filed Feb. 9, 2004 now abandoned. The contents of application Ser. No. 10/774,665 are incorporated herein by reference.

FIELD OF THE INVENTION

The present invention pertains generally to interventional catheters that are to be advanced into the vasculature of a patient, and to methods for manufacturing such catheters. More particularly, the present invention pertains to catheters that include controllable elements for bending the catheter during the advancement and placement of the catheter in the vasculature. The present invention is particularly, but not exclusively, useful as an articulation segment for a catheter that allows the catheter to bend in a plurality of different planes.

BACKGROUND OF THE INVENTION

During the advancement of a catheter into the vasculature of a patient, there are several factors that must be taken into consideration. One of the more important considerations is the ability of the catheter to be accurately and properly guided through the vasculature into its intended location or position. An important adjunct of this is the ability of the catheter to be properly configured, if necessary, once it has been properly positioned. In some instances, such as when an over-the-wire catheter is being used, the guideability of the catheter is dependent on the proper pre-positioning of the guidewire in the vasculature. This is not so with other types of catheters. For instance, due to its unique functional refrigeration requirements, a cryocatheter must typically be positioned in the vasculature without the assistance of a guidewire. Furthermore, many catheters, such as cryocatheters, may need to be reconfigured once they have been positioned in the vasculature.

The need for being able to guide a catheter through the vasculature, without the assistance of a guidewire, has been recognized. Heretofore, however, systems for accomplishing this have relied on the catheter's ability to bend in a predetermined plane, and on its ability to be rotated so that the predetermined bending plane can be properly oriented. For example, U.S. Pat. No. 2,574,840 for an invention entitled "Flexible Medical Probe" which issued to Pieri et al., as well as U.S. Pat. No. 5,114,414 which issued to Buchbinder for an invention entitled "Low Profile Steerable Catheter," both disclose systems for concertedly deflecting the tip, and rotating the body, of a catheter/probe to steer the catheter/probe through the vasculature of a patient.

It happens that, in addition to the ability to guide a catheter through the vasculature, more control over the catheter may be required. New procedures are now being perfected wherein it is necessary for the catheter to be reconfigured after it has been properly positioned in the vasculature. For example, in order to treat atrial fibrillation by cryoablating tissue, it is desirable to configure the tip of the catheter as a ring that can be placed in contact with tissue at an ostium where a pulmonary vein connects with the left atrium. Then, after the tissue around the ostium has been cryoablated, the catheter must again be reconfigured for withdrawal from the vasculature. In this procedure, as in others not mentioned here, there is a need for a catheter that has extensive flexibility for changing configurations.

In light of the above, it is an object of the present invention to provide an articulating segment for a catheter that allows the catheter to be selectively bent in any of several planes without rotating the catheter. Another object of the present invention is to provide an articulating segment for a catheter that allows the catheter to be simultaneously bent in different planes to effectively reconfigure the catheter, as desired. Still another object of the present invention is to provide an articulating segment for a catheter that can bend with a relatively small radius of curvature. Another object of the present invention is to provide an articulating segment for a catheter that can bend into a ring-shaped configuration. Yet another object of the present invention is to provide an articulating segment for a catheter, and a method for its manufacture, that is simple to implement, easy to use, and comparatively cost effective.

SUMMARY OF THE INVENTION

In accordance with the present invention, an articulation segment for a catheter includes an elongated hollow tube that has a wall and that defines a longitudinal axis. For the present invention, the tube is formed with a first plurality of slits that are cut through the wall and oriented in respective planes that are substantially perpendicular to the axis. Further, each slit extends azimuthally in an arc partway around the axis and each has a center and a substantially same arc length. The respective centers of these slits are aligned with each other in a centerline that is substantially parallel to the axis. Preferably, the tube is a stainless steel hypotube, and the cuts are made through the wall of the tube with widths in a range of approximately ten to five hundred microns. For the present invention this cutting is preferably done using a laser cutting system.

The tube of the present invention also has a second plurality of slits that are formed in substantially the same manner as the first plurality of slits. For a preferred embodiment of the present invention, however, the centerline of the second plurality of slits is diametrically opposed to the centerline of the first plurality of slits. Further, the slits of the first plurality are axially offset from the slits of the second plurality. Thus, as each slit of both the first and second pluralities has a first end and a second end, their respective ends preferably overlap each other. Specifically, the first end of each slit in the first plurality of slits is juxtaposed and overlaps with the second end of adjacent slits in the second plurality of slits. Likewise, the second end of each slit in the first plurality of slits is juxtaposed and overlaps with the first end of an adjacent slit in the second plurality of slits.

In the preferred embodiment of the present invention, all of the slits have a substantially same arc length. Generally, this arc length will be greater than one hundred and eighty degrees. Accordingly, the respective ends of the slits in the first and second pluralities of slits will overlap. Preferably, this overlap will be through an arc distance of approximately ten degrees.

In an alternate embodiment of the present invention the first plurality of slits comprise a first set of slits and the second plurality of slits comprise a second set of slits. For this alternate embodiment the tube is further formed with a third set of slits that are coplanar with, and diametrically opposed to, the first set of slits. Further the tube is formed with a fourth set of slits that are coplanar with, and diametrically opposed to, the second set of slits. In this embodiment, the slits in all four sets have a substantially same arc length that is greater than ninety degrees, but less than one hundred and eighty degrees.

As intended for the present invention, within each plurality or set of slits, all of the slits are aligned along a common centerline and they all have a common azimuthal arc length and orientation. For the embodiment of the present invention having only two pluralities or sets of slits, the slits of one plurality are axially offset from the slits of the other plurality and their respective centerlines are azimuthally offset from each other. For the alternate embodiment having four different pluralities or sets of slits, the corresponding slits of diametrically opposed sets are coplanar to each other and are axially offset from the other pair of diametrically opposed sets. In the alternate embodiment, however, the centerlines of adjacent sets are azimuthally offset from each other by an angle of ninety degrees. For either embodiment, the result is a catheter having an articulation segment that is capable of selectively bending the catheter in a plurality of planes.

In a particular embodiment of the articulation segment, the segment includes a first section having slits arranged as described above for bending in a first plane, a second section having slits arranged as described above for bending in a second plane (e.g. normal to the first plane), and a transition section positioned between the first and second sections. In greater detail, the transition section includes a plurality of first slits and a plurality of second slits. The slits are cut in respective planes that are substantially perpendicular to the tube axis and all have a substantially same arc length, which is typically greater than one hundred and eighty degrees.

For the transition section, each first slit is azimuthally offset from an adjacent first slit. Similarly, each second slit is azimuthally offset from an adjacent second slit. With this cooperation of structure, the respective centers of the first slits are aligned along a first substantially helical path. Similarly, the respective centers of the second slits are aligned along a second substantially helical path, with the first helical path being substantially diametrically opposed to the second helical path. With this slit arrangement, the articulation segment can be reconfigured from a straight, substantially cylindrically shaped tube to a configuration in which a portion of the articulation segment is formed in the shape of a ring that is oriented in a plane that is somewhat perpendicular to the original axis.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of an articulation segment in accordance with the present invention;

FIG. 2 is a perspective view of a portion of the articulation segment shown in FIG. 1 with portions shown in phantom;

FIG. 3 is a schematic illustration of relative arc lengths and distances pertinent to the articulation segment as shown in FIG. 1 and FIG. 2;

DESCRIPTION OF THE PREFERRED EMBODIMENTS

Figure 4:
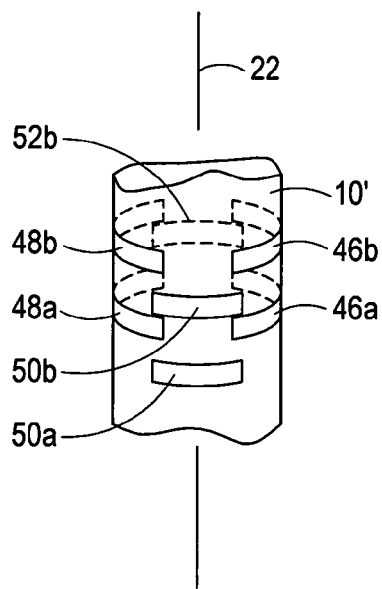
FIG. 4 is a perspective view of a portion of an alternate embodiment of the articulation segment with portions shown in phantom.

Referring initially to FIG. 1, an articulation segment in accordance with the present invention is shown and generally designated 10. As shown, the articulation segment 10 includes an elongated hollow tube 12 that is formed by a wall 14. In detail, the wall 14 of articulation segment 10 has an outer surface 16, and it has an inner surface 18 that surrounds a lumen 20. As indicated in FIG. 1, when in a straightened configuration, the tube 12 defines a longitudinal axis 22. Preferably, the tube 12 is made of a thermally conductive, rigid material, such as stainless steel, that permits the tube 12 to be rotated around the axis 22.

By cross-referencing FIG. 1 with FIG. 2, it will be appreciated that the tube 12 of articulation segment 10 is formed with a first plurality of slits 24, of which the slits 24a and 24b are exemplary. It also has a second plurality of slits 26, of which the slits 26a and 26b are exemplary. Further, the slits 24 have centers 28 (e.g. centers 28a and 28b) and the slits 26 have centers 30 (e.g. centers 30a and 30b) that are respectively midway between the ends of the slits 24, 26. As best appreciated by referencing FIG. 2 with FIG. 3, all of the slits 24 have a substantially same arc length 32 (measured in degrees) and all of the slits 26 have a substantially same arc length 34 (also measured in degrees). Importantly, for the embodiment of the articulation segment 10 shown in FIGS. 1 and 2, the arc lengths 32 and 34 are each approximately greater than one hundred and eighty degrees. Thus, as schematically indicated in FIG. 3, the ends of the slits 24 and 26 will overlap each other through an arc distance 36a or 36b. Preferably, the arc distances 36a and 36b will each be about ten degrees.

In both FIGS. 1 and 2, the slits 24 and 26 are shown to lie in respective planes that are substantially perpendicular to the axis 22. Also, the centers 28 of slits 24 are azimuthally oriented and aligned with each other along a centerline 38, while the centers 30 of slits 26 are similarly oriented and aligned with each other along a centerline 40. As shown in FIG. 2, the centerline 38 is diametrically opposed to the centerline 40. Thus, due to the opposition of their respective centerlines 38 and 40, the slits 24 are azimuthally offset from the slits 26. Also, as evidenced by the overlapping of their respective ends, the slits 24 and slits 26 are axially offset from each other.

As envisioned for the present invention, the plurality of slits 24 (i.e. a set) and the plurality of slits 26 (i.e. a set) will all be cut into the tube 12 by a laser system (not shown). For the embodiment of the articulation segment 10 shown in FIGS. 1 and 2, the slits 24 and 26 extend azimuthally partway around the axis 22 and, preferably, they will have respective widths 42 and 44 that are in a range of from approximately ten to five hundred microns. Also, the axial offset distance 45 between adjacent slits of different sets (e.g. the axial distance 45 between slit 24a and slit 26a in FIG. 1, or FIG. 2) will be in a range of from approximately 200 microns to about 5 millimeters. It will be appreciated, however, that the widths 42, 44 and the axial distances 45 can be varied as required and may fall outside the above-stated ranges.

In alternate embodiments of the present invention, there can be three, four or, perhaps even more different sets of slits that are appropriately offset axially and azimuthally from each other. For example, in FIG. 4, the alternate embodiment of an articulation segment 10' is shown having four different sets of slits. Specifically, a first set (represented by slits 46a and 46b) are shown diametrically opposed, but coplanar, with a second set (represented by slits 48a and 48b). Similarly, a third set (represented by slits 50a and 50b) are shown diametrically opposed, and coplanar, with a fourth set (represented by the slit 52b). Since each set of slits (e.g. slits 46) is coplanar with another set of slits (e.g. slits 48), the arc lengths of the slits in articulation segment 10' must necessarily be less than one hundred and eighty degrees. Preferably, in order to achieve some overlap (e.g. slit 50a overlaps with both slit 46a and slit 48a) the various slits for the alternate embodiment articulation segment 10' will have respective arc lengths in a range that is greater than ninety degrees, but less than one hundred and eighty degrees.

Figure 5A:
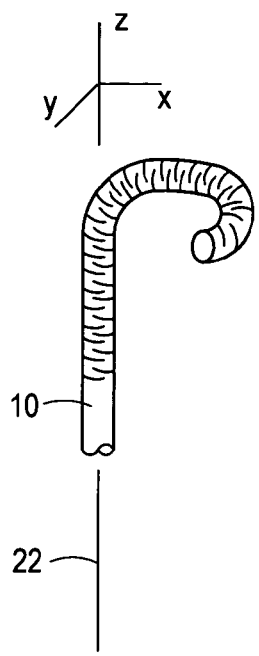
FIG. 5A is a perspective view of an articulation segment of the present invention being bent in an x-z plane and an x-y plane.
Figure 5B:
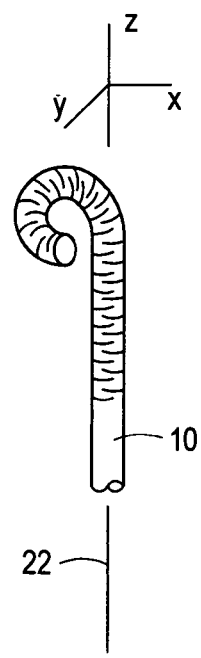
FIG. 5B is a perspective view of an articulation segment of the present invention being bent in an y-z plane and an x-y plane.

For the operation of the present invention, the arrangements of the slits disclosed above allows the articulation segment 10 to be bent simultaneously in different planes. For instance, FIG. 5A shows the articulation segment 10 being bent both in the x-y plane and in the x-z plane. On the other hand, FIG. 5B shows the same articulation segment 10 being bent both in the x-y plane and in the y-z plane. As intended for the present invention, other planar orientations are also possible. The controls for establishing these various orientations for the articulation segment 10 will be dependent on the desires and needs of the operator.

Figure 6:
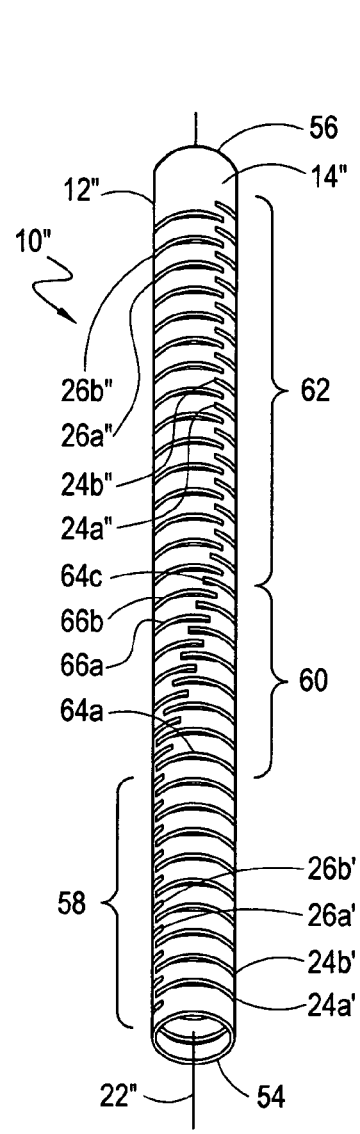
FIG. 6 is a perspective view of a portion of yet another embodiment of the articulation segment.

FIG. 6 shows another embodiment of an articulation segment (generally designated 10") with alternating cuts. As shown, the articulation segment 10" includes an elongated hollow tube 12" that is formed by a wall 14" and extends from a first tube end 54 to a second tube end 56. FIG. 6 shows the tube 12" in a straightened configuration, a configuration in which the tube 12" defines a longitudinal axis 22". It can be further seen from FIG. 6 that the tube 12" consists of three somewhat distinct axial sections 58, 60, 62.

By cross-referencing FIG. 6 with FIG. 2, it will be appreciated that the section 58 of the articulation segment 10" is formed with a first plurality of slits 24', of which the slits 24a' and 24b' are exemplary. Section 58 also has a second plurality of slits 26', of which the slits 26a' and 26b' are exemplary. Further, it is to be appreciated that the slits 24' have centers 28 (see FIG. 2) and the slits 26' have centers 30 (see FIG. 2) that are respectively midway between the ends of the slits 24', 26'. Like the embodiment shown in FIG. 1, section 58 of the articulation segment 10" is formed with slits 24' and slits 26' which all have a substantially same arc length, which for the embodiment shown in FIG. 6, is greater than one hundred and eighty degrees.

Continuing with FIG. 6, it can be seen that the slits 24' and 26' in section 58 are cut in respective planes that are substantially perpendicular to the axis 22". Also, like the embodiment shown in FIGS. 1 and 2, the centers of slits 24' are azimuthally oriented and aligned with each other along a first common centerline and the centers of slits 26' are oriented and aligned with each other along a second common centerline, with the first and second centerlines being diametrically opposed. Thus, due to the opposition of their respective centerlines, the slits 24' are azimuthally offset from the slits 26'. Also, as evidenced by the overlapping of their respective ends, the slits 24' and slits 26' are axially offset from each other.

FIG. 6 also shows that the section 62 of the articulation segment 10" is formed with a first plurality of slits 24", of which the slits 24a" and 24b" are exemplary and a second plurality of slits 26", of which the slits 26a" and 26b" are exemplary. Further, it is to be appreciated that the slits 24" have centers 28 (see FIG. 2) and the slits 26" have centers 30 (see FIG. 2) that are respectively midway between the ends of the slits 24", 26". Like the embodiment shown in FIGS. 1 and 2, the slits 24" and slits 26" in section 62 of the articulation segment 10" all have a substantially same arc length, which for the embodiment shown in FIG. 6, is greater than one hundred and eighty degrees.

Comparing FIG. 6 with FIG. 2, it can be seen that the slits 24" and 26" in section 62 are cut in respective planes that are substantially perpendicular to the axis 22". Also, like the embodiment shown in FIGS. 1 and 2, the centers of slits 24" are azimuthally oriented and aligned with each other along a first common centerline and the centers of slits 26" are oriented and aligned with each other along a second common centerline, with the first and second centerlines being diametrically opposed. Thus, due to the opposition of their respective centerlines, the slits 24" are azimuthally offset from the slits 26". Also, as evidenced by the overlapping of their respective ends, the slits 24" and slits 26" are axially offset from each other.

A comparison of section 58 with section 62 of the articulation segment 10" reveals that the slits 24" in section 62 are azimuthally offset from the slits 24' in section 58 by approximately ninety degrees. Similarly, it can be seen from FIG. 6 that the slits 26" in section 62 are azimuthally offset from the slits 26' in section 58 by approximately ninety degrees. As detailed further below, the ninety degree azimuthal offset between section 58 and section 62 allows section 62 to bend in a different plane than section 58. To accommodate these different bend planes, the articulation segment 10" includes a transition section (i.e. section 60) that is positioned between section 58 and section 62.

Figure 7:
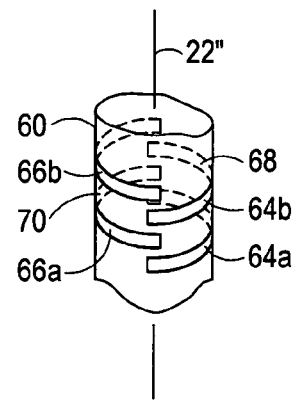
FIG. 7 is a perspective view of a portion of the articulation segment shown in FIG. 6 with portions shown in phantom.

A better understanding of the transition section 60 can be obtained with cross-reference to FIGS. 6 and 7. As seen there, the transition section 60 is formed with a first plurality of slits 64, of which the slits 64a and 64b are exemplary and a second plurality of slits 66, of which the slits 66a and 66b are exemplary. Each slit 64 has a center 68, and similarly, each slit 66 has a center 70, with centers 68, 70 located respectively midway between the ends of the slits 64, 66. As best seen in FIG. 7, the slits 64 and slits 66 are cut in respective planes that are substantially perpendicular to the axis 22" and all have a substantially same arc length, which is typically greater than one hundred and eighty degrees, as shown.

With continued reference to FIGS. 6 and 7, it can be seen that each slit 64 is azimuthally offset from an adjacent slit 64. For example, as shown in FIG. 7, slit 64a is azimuthally offset from adjacent slit 64b. Similarly, each slit 66 is azimuthally offset from an adjacent slit 66. For example, as shown in FIG. 7, slit 66a is azimuthally offset from adjacent slit 66b. As best seen in FIG. 6, the plurality of slits 64 includes an initial slit 64a and a final first slit 64c and it can be seen that the center of the initial slit 64a is azimuthally offset from the center of the final slit 64c by approximately ninety degrees. FIGS. 6 and 7 further show that the respective centers 68 of the slits 64 are aligned along a first substantially helical path. Similarly, the respective centers 70 of the slits 66 are aligned along a second substantially helical path, and it can be seen that the first helical path is substantially diametrically opposed to the second helical path. Thus, due to the opposition of their respective helical center paths, each slit 64 is azimuthally offset from an adjacent slit 66. Also, as evidenced by the overlapping of their respective ends, the slits 64 and slits 66 are axially offset from each other.

Figure 8:
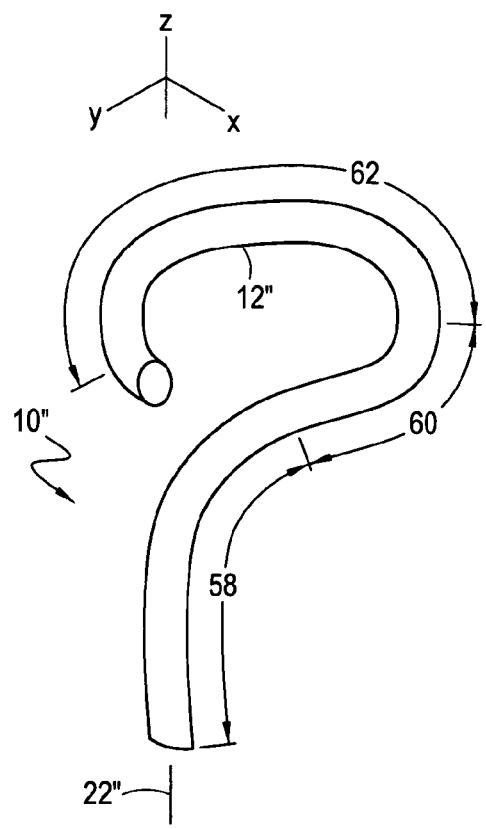
FIG. 8 is a perspective view of the articulation segment shown in FIG. 6 after being bent to reconfigure a portion of the segment into a ring shape.

For the operation of the articulation segment 10", the arrangements of the slits 24', 26', 64, 66, 24", 26" allows the segment 10" to be bent simultaneously in different planes as shown in FIG. 8. Specifically, as shown, the segment 10" can be reconfigured from the straight, substantially cylindrically shaped tube shown in FIG. 6 to the configuration shown in FIG. 8. The reconfiguration can be accomplished, for example, by drawing the tube end 56 toward the tube end 54 with a pull wire (not shown) attached to one of the ends 54, 56. As FIG. 8 shows, when reconfigured, a portion of the tube 12" is formed in the shape of a ring that is oriented in a plane that is somewhat perpendicular to the original axis 22". This ring shaped portion can be used, for example, to simultaneously contact an annular shaped portion of tissue surrounding a vessel. In one application of the articulation segment 10", the ring shaped portion can be used to contact and cryoablate the tissue surrounding an ostium where a pulmonary vein connects to the left atrium. This cryoablation procedure can be used to form a conduction block to prevent irregular electrical signals from entering the heart and causing atrial fibrillation.

While the particular Catheter Articulation Segment With Alternating Cuts as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for configuring a catheter tube as a ring, wherein the catheter tube comprises:
    a distal section biased to bend in a plane around a first axis to form the ring in a plane substantially perpendicular to the first axis; and
    a transition section having a first end and a second end, with the first end of the transition section being connected to the distal section, wherein the transition section is helically biased to move between a first configuration wherein the transition section is substantially straight to define a base line oriented substantially perpendicular to the first axis, and a second configuration wherein the first axis of the distal section is substantially aligned parallel with the base line;
    wherein the catheter tube has a wall and defines a longitudinal axis, and the transition section is formed with a plurality of first slits cut through the wall in respective planes substantially perpendicular to the longitudinal axis, with each first slit extending azimuthally in an arc partway around the axis from a first end to a second end and defining a center midway therebetween, and wherein the respective centers of the first slits are aligned along a first substantially helical path, the tube being further formed with a plurality of second slits cut through the wall in respective planes substantially perpendicular to the axis, with each second slit extending azimuthally in an arc partway around the axis from a first end to a second end and defining a center midway therebetween, and wherein the respective centers of the second slits are aligned along a second substantially helical path, with each said first slit being located between a pair of adjacent second slits and each said second slit being located between a pair of adjacent first slits, and with said second helical path being substantially diametrically opposite said first substantially helical path relative to said axis to allow for the selective helical bending of the transition section.

2. A device as recited in claim 1 wherein each first slit is azimuthally offset from an adjacent first slit and further including an initial first slit and a final first slit and wherein the center of the initial first slit is azimuthally offset from the center of the final first slit by approximately ninety degrees.

3. A device as recited in claim 2 wherein the first end of each first slit is juxtaposed and overlaps with the second end of an adjacent second slit, and the second end of each first slit is juxtaposed and overlaps with the first end of an adjacent second slit.

4. A device as recited in claim 3 wherein each first slit and each second slit has a substantially same arc length, and wherein the arc length is greater than one hundred and eighty degrees.

5. A device for configuring a catheter tube as a ring, wherein the catheter tube comprises:
    a distal section biased to bend in a plane around a first axis to form the ring in a plane substantially perpendicular to the first axis;
    a proximal section biased to bend in a plane around a second axis; and
    an transition section interconnecting the distal section with the proximal section, wherein the transition section is helically biased to move the first axis of the distal section between a first configuration wherein the first axis is substantially parallel to the second axis of the proximal section and a second configuration wherein the first axis is substantially perpendicular to the second axis of the proximal section;
    wherein the catheter tube has a wall and defines a longitudinal axis, and the transition section is formed with a plurality of first slits cut through the wall in respective planes substantially perpendicular to the longitudinal axis, with each first slit extending azimuthally in an arc partway around the axis from a first end to a second end and defining a center midway therebetween, and wherein the respective centers of the first slits are aligned along a first substantially helical path, the tube being further formed with a plurality of second slits cut through the wall in respective planes substantially perpendicular to the axis, with each second slit extending azimuthally in an arc partway around the axis from a first end to a second end and defining a center midway therebetween, and wherein the respective centers of the second slits are aligned along a second substantially helical path, with each said first slit being located between a pair of adjacent second slits and each said second slit being located between a pair of adjacent first slits, and with said second helical path being substantially diametrically opposite said first substantially helical path relative to said axis to allow for the selective helical bending of the transition section.

6. A device as recited in claim 5 wherein the proximal section is formed with a plurality of first proximal slits each having a center and with a plurality of second proximal slits each having a center, with each said first proximal slit being located between a pair of adjacent second proximal slits and each said second proximal slit being located between a pair of adjacent first proximal slits, with each plurality of proximal slits cut into the tube through the wall in planes substantially perpendicular to the axis, with the respective centers of the first proximal slits aligned along a first proximal line substantially parallel to the axis, and with the respective centers of the second proximal slits aligned along a second proximal line substantially parallel to the axis and diametrically opposed to the first proximal line, and wherein the distal section is axially spaced from said proximal section and formed with a plurality of first distal slits each having a center and with a plurality of second distal slits each having a center, with each said first distal slit being located between a pair of adjacent second distal slits and each said second distal slit being located between a pair of adjacent first distal slits, with each plurality of distal slits cut into the tube through the wall in planes substantially perpendicular to the axis, with the respective centers of the first distal slits aligned along a first distal line substantially parallel to the axis and azimuthally offset from said first proximal line, and with the respective centers of the second distal slits aligned along a second distal line substantially parallel to the axis, diametrically opposed to the first distal line and azimuthally offset from the second proximal line.

7. A device as recited in claim 4 wherein the respective ends of the first slits and the second slits overlap through an arc distance of approximately ten degrees.

8. A device as recited in claim 1 wherein each of the first slits and each of the second slits has a width that is no greater than ten microns.

9. A device as recited in claim 1 wherein each of the first slits and each of the second slits has a width that is at least five microns.

10. A device as recited in claim 1 wherein the catheter tube is a hypotube.

11. A device as recited in claim 1 wherein the catheter tube is formed from stainless steel.

* * * * *

UNITED STATES PATENT AND TRADEMARK OFFICE
CERTIFICATE OF CORRECTION

PATENT NO. : 7,637,903 B2  Page 1 of 1
APPLICATION NO. : 10/872612
DATED : December 29, 2009
INVENTOR(S) : Lentz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 530 days.

Signed and Sealed this

Ninth Day of November, 2010

David J. Kappos
*Director of the United States Patent and Trademark Office*